United States Patent
Brunner et al.

(10) Patent No.: US 10,806,706 B2
(45) Date of Patent: *Oct. 20, 2020

(54) STORAGE-STABLE FORMULATIONS

(71) Applicant: DSM IP ASSETS B.V., Heerlen (NL)

(72) Inventors: Dominik Josef Brunner, Kaiseraugst (CH); Laure Clasadonte, Kaiseraugst (CH); Christine Gothscheck, Kaiseraugst (CH); Olivia Brigitte Vidoni, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/485,560

(22) PCT Filed: Feb. 9, 2018

(86) PCT No.: PCT/EP2018/053337
§ 371 (c)(1),
(2) Date: Aug. 13, 2019

(87) PCT Pub. No.: WO2018/149756
PCT Pub. Date: Aug. 23, 2018

(65) Prior Publication Data
US 2020/0046649 A1 Feb. 13, 2020

(30) Foreign Application Priority Data

Feb. 14, 2017 (EP) .................... 17156107

(51) Int. Cl.
| A61K 31/04 | (2006.01) |
| A61K 9/16 | (2006.01) |
| A61K 47/44 | (2017.01) |
| A23K 50/10 | (2016.01) |
| A23K 20/111 | (2016.01) |
| A23K 20/132 | (2016.01) |
| A23K 20/10 | (2016.01) |
| A23K 20/28 | (2016.01) |

(52) U.S. Cl.
CPC ............ A61K 31/04 (2013.01); A61K 9/1611 (2013.01); A61K 47/44 (2013.01)

(58) Field of Classification Search
None
See application file for complete search history.

(56) References Cited

U.S. PATENT DOCUMENTS

| 4,775,540 A | 10/1988 | Hertel et al. |
| 2007/0254070 A1 | 11/2007 | Epouse et al. |
| 2019/0343149 A1* | 11/2019 | Gadient ................. A23K 40/30 |

FOREIGN PATENT DOCUMENTS

WO 2012/084629 6/2012

OTHER PUBLICATIONS

Sepiolite NPL Google search (2 pages); downloaded Apr. 7, 2020.*
Chem Draw structures of claim 5 (1 pg); searched and downloaded Apr. 7, 2020.*
NPL search results: IQQueryQuick Export—202006092044.pdf.; downloaded Jun. 9, 2020.*
NPL search results: IQQueryQuick Export—202006092047.pdf.; downloaded Jun. 9, 2020.*
International Search Report for PCT/EP2018/053337 dated Apr. 26, 2018, 2 pages.

* cited by examiner

Primary Examiner — Jeffrey T. Palenik
(74) Attorney, Agent, or Firm — Nixon & Vanderhye P.C.

(57) ABSTRACT

The present invention relates to storage-stable formulations of 3-nitrooxypropanol and derivatives thereof as well as to the production of such formulations.

20 Claims, No Drawings

STORAGE-STABLE FORMULATIONS

This application is the U.S. national phase of International Application No. PCT/EP2018/053337 filed Feb. 9, 2018 which designated the U.S. and claims priority to EP Patent Application No. 17156107.9 filed Feb. 14, 2017, the entire contents of each of which are hereby incorporated by reference.

The present invention relates to storage stable formulations of 3-nitrooxypropanol and derivatives thereof as well as to the production of such formulations.

The temperature of the air surrounding the earth is increasing, a process referred to as global warming. One of the main focuses to reduce this warming effect is to reduce the amount of greenhouse gases emitted into the atmosphere. Greenhouse gases are emitted from several different sources, both natural and artificial; however, the two sources with the most emphasis are the agricultural and fossil fuel industries. Within agriculture, ruminants and in particular cattle are the major contributors to the biogenic methane formation, and it has been estimated that the prevention of methane formation from ruminants would almost stabilize atmospheric methane concentrations.

3-Nitrooxy propanol and structural analogues thereof have been reported to be highly efficient in reducing the formation of methane in ruminants without affecting microbial fermentation in a way that would be detrimental to the host animal (WO2012/084629).

However, 3-nitrooxypropanol and structural analogues thereof have been found not to be effectively retained in standard carrier systems commonly used in the feed industry such as diatomaceous earth or silica in general under conventional storage conditions.

Thus, there is an ongoing need to develop a product form, which overcomes the abovementioned storage problem, i.e. a product form which avoids the evaporation of 3-nitrooxypropanol during storage, and additionally has a good flowability and can easily be admixed with other components commonly used in feed products for ruminants.

Surprisingly, it has been found that 3-nitrooxypropanol is more effectively retained in silica having an average particle size of ≤320 μm compared to silica having a larger particle size under conventional storage conditions.

Thus, in a first embodiment the present invention relates to powderous formulation (I) comprising (i) At least 0.1 weight-% (wt-%), based on the total weight of the powderous formulation, of a compound of formula (I)

formula (I)

wherein
n is an integer from 1 to 15
$R^1$ is selected from the group consisting of H, $C_1$-$C_6$alkyl, phenyl, —OH, —$NH_2$, —CN, —COOH, —O(C═O)$R^8$, —NHC(═O)$R^8$, $SO_2NHR^8$, and —$ONO_2$, and
$R^8$ is $C_1$-$C_6$alkyl, phenyl, pyridyl such as preferably 2-pyridyl
with the proviso that when n is >3 the hydrocarbon chain may be interrupted by —O— or —NH—.

(ii) 0 to 40 wt-%, based on the total weight of the powderous formulation, of an edible solvent, and (iii) at least 25 wt-%, based on the total weight of the powderous formulation, of silica having an average particle size D(v, 0.5)≤320 μm.

It is well understood that the compositions according to the present invention are storage-stable, i.e. exhibit a retention of at least 80%, preferably of at least 85% most preferably of at least 87% of the compound of formula (I).

The formulations according to the present invention are powders, which depending on the process of production as well as the storage conditions, the may comprise some water. The water content is usually below 7 wt-%, based on the total weight of the formulation. Therefore, a further embodiment of the present invention relates to formulations as described above, wherein 0 to 7 wt-%, based on the total weight of the formulation, of water is present.

The formulations according to the present invention may furthermore contain small amounts of customary additives commonly used in the preparation of powderous formulations for feed application. Therefore, a further embodiment of the present invention relates to formulations according to the present invention, wherein 0 to 5 wt-%, based on the total weight of the formulation, of an additive is present.

It is clear that in all embodiments of the present invention the addition of all the wt.-% always adds up to 100. However, it cannot be excluded that small amount of impurities or additives may be present such as e.g. in amounts of less than 5 wt.-%, preferably less than 3 wt.-% which are e.g. introduced via the respective raw materials or processes used.

Particular advantageous compounds of formula (I) in all embodiments of the present invention are compounds of formula (II) wherein n is an integer between 3 and 9 and $R^1$ is OH, COOH or —$ONO_2$ and with the proviso that if n is 4 the hydrocarbon chain may be interrupted by —NH— such as in particular the compounds of formula (II) $R^1$—$(CH_2)_2$—NH—$(CH_2)_2$—$ONO_2$ (II). Even more preferred are compounds of formula (I) wherein n is an integer between 3 and 9 and $R^1$ is OH, COOH or —$ONO_2$.

Even more advantageous compounds of formula (I) in all embodiments of the present invention are 3-nitrooxypropanol (CAS-No: 100502-66-7), 9-nitrooxynonanol, 5-nitroxy pentanoic acid (CAS 74754-56-6), 6-nitroxy hexanoic acid (CAS 74754-55-5), bis(2-hydroxyethyl)amine dinitrate (CAS 20830-49-3), 1,4-bis-nitrooxybutane (CAS 3457-91-8) and 1,5-bis-nitrooxypentane (CAS 3457-92-9). Most preferred in all embodiments of the present invention is 3-nitrooxypropanol.

The compounds of formula (I) preferably have a boiling point below 250° C. at 760 Torr, preferably a boiling point between 100 and 200° C. at 760 Torr.

The compounds according to the present invention are known and either commercially available or can be prepared in analogy to the processes as e.g. disclosed in WO2012/084629.

Silica is a well-known carrier material in the feed and food industry and refers to white microspheres of amorphous silica (also referred to as silicone dioxide) and is available in a great variety of particle sizes. Particular suitable silica according to the present invention is amorphous precipitated silica having a particle size of ≤320 μm such as e.g. Ibersil D-250 from IQE Group, Sipernat 2200 from Evonik or Tixosil 68 from Solvay.

Preferably in all embodiments of the present invention the silica according to the present invention has an average (mean) particle size D(v, 0.5) selected in the range of 100 to 320 μm, more preferably in the range of 200 to 310 μm and most preferably in the range of 200 to 300 μm.

The particle sizes as given herein are measured by a Malvern Master Sizer 2000 following the recommendations outlined in ISO13320-1 for particle size analysis via laser diffraction methods (laser diffraction light scattering). During this laser diffraction measurement, particles are passed through a focused laser beam. The particles scatter light at an angle that is inversely proportional to their size. The angular intensity of the scattered light is then measured by a series of photosensitive detectors. The map of scattering intensity versus angle is the primary source of information used to calculate the particle size. For the measurement of the silica according to the present invention a dry powder feeder (Malvern Scirocco) was used.

Advantageously, the silica according to the present invention furthermore exhibits a pH selected in the range of pH 6 to 7 (measured as a 1% suspension in distillated water) as this further increases the retention of the active.

The term edible oil refers to oils commonly used in feed applications. Preferred edible oils in all embodiments of the present invention are propyleneglycol, corn oil, rapeseed oil, sunflower oil, middle chain triglyceride (MCT) and glycerol as well as mixtures thereof. Most preferred in all embodiments of the present inventions is the use of propyleneglycol.

The term additive as used herein refers to additives commonly used in the preparation of powderous formulations for feed application such as in particular to thickeners, such as in particular gums or cellulose derivatives such as xanthan gum, karaya gum and/or ethylcellulose.

Preferred embodiments of the present invention are formulations (I) which are formulations (II), which comprise
(i) 1 to 25 wt-%, based on the total weight of the powderous formulation, of a compound of formula (I), and
(ii) 5 to 45 wt-%, based on the total weight of the formulation, of at least one edible oil, and
(iii) at least 30 wt-%, based on the total weight of the powderous formulation, of silica having a D(v, 0.5) of ≤320 μm, and
(iv) 0 to 10 wt-%, based on the total weight of the powderous formulation, of water and/or an additive.

A more preferred embodiment of the present invention relates to a formulation (III) consisting of
(i) 2 to 20 wt-%, based on the total weight of the powderous formulation, of a compound of formula (I), and
(ii) 10 to 45 wt-%, based on the total weight of the powderous formulation, of an edible oil, and
(iii) at least 35 wt-%, based on the total weight of the powderous formulation, of silica having a D(v, 0.5) of ≤320 μm, and
(iv) 0 to 10 wt-%, based on the total weight of the powderous formulation, of water and/or an additive.

An especially preferred embodiment of the present invention relates to a formulation (IV) consisting of
(i) 2 to 15 wt-%, based on the total weight of the powderous formulation, of a compound of formula (I), and
(ii) 20 to 40 wt-%, based on the total weight of the powderous formulation, of an edible oil, and
(iii) at least 35 wt-%, based on the total weight of the powderous formulation, of silica having a D(v, 0.5) of ≤320 μm, and
(iv) 0 to 5 wt-%, based on the total weight of the powderous formulation, of of water and/or an additive.

A very specific formulation of the present invention is a formulation (V) consisting of
(i) 2 to 12 wt-%, based on the total weight of the powderous formulation, of 3-nitrooxypropanol, and
(ii) 20 to 40 wt-%, based on the total weight of the powderous formulation, of propyleneglycol, and
(iii) at least 40 wt-%, based on the total weight of the powderous formulation, of silica having a D(v, 0.5) of ≤320 μm, and
(iv) 0 to 7 wt-%, based on the total weight of the powderous formulation, of water.

Generally, to produce a powder according to the present invention (formulations (I), (II), (III), (IV), (V)) the compound of formula (I) is, optionally diluted in the edible oil and further optionally admixed with the additive(s), sprayed onto or admixed with a silica according to the present invention.

It is also possible that the compound of formula (I) is, optionally in the presence of an edible oil and further optionally admixed with the additive(s), diluted in an organic solvent suitable for the preparation of food or feed products such as e.g. dichloromethane, sprayed onto or admixed with silica followed by evaporation of the organic solvent.

The powderous formulation according to the present invention can additionally be coated with customary coatings in the art such as wax or fats. If present, such coating is generally applied in amounts of 5 to 50 wt.-% based on the total weight of the powderous form. Advantageously, the coating comprises at least one wax and/or at least one fat, which has a dropping point of from 30 to 85° C.

The dropping point of a material as used herein refers to the temperature (in ° C.) when the material begins to melt under standardized conditions. Thus the material is heated so long until it changes the state of matter from solid to liquid. The dropping point is the temperature when the first dropping is released from the material. The determination of the dropping point (Tropfpunkt) is carried out as described in the standard norm DIN ISO 2176.

Particularly suitable waxes to be used as coating in the context of the present invention include organic compounds consisting of long alkyl chains, natural waxes (plant, animal) which are typically esters of fatty acids and long chain alcohols as well as synthetic waxes, which are long-chain hydrocarbons lacking functional groups.

Particularly suitable fats to be used as coating in the context of the present invention include a wide group of compounds which are soluble in organic solvents and largely insoluble in water such as hydrogenated fats (or saturated fats) which are generally triesters of glycerol and fatty acids. Suitable fats can have natural or synthetic origin. It is possible to hydrogenate a (poly)unsaturated fat to obtain a hydrogenated (saturated) fat.

Preferred examples of waxes and fats to be used as coating according to the present invention are glycerine monostearate, carnauba wax, candelilla wax, sugarcane wax, palmitic acid, stearic acid hydrogenated cottonseed oil, hydrogenated palm oil and hydrogenated rapeseed oil as well as mixtures thereof.

All the above disclosed formulations (I), (II), (III), (IV), (V) can be used as such or in feed products.

Additionally, all the above disclosed formulations (I), (II), (III), (IV) and (V) can be used as such in the production of feed products.

In another embodiment, the invention relates to the use of silica having an average particle size D(v, 0.5) of ≤320 μm, preferably having a D(v, 0.5) selected in the range of 100 to 320 μm, more preferably in the range of 200 to 310 μm and most preferably in the range of 200 to 300 μm to enhance the retention of a compound of formula (I) with all the preferences and definitions as given herein. Preferably, the retention is at least 80%, preferably at least 50% most preferably at least 87%. In a particular preferred embodiment, the silica furthermore exhibits a pH selected in the range of pH 6 to 7 (measured as a 1% suspension in distilled water) as this further increases the retention of the active.

In another embodiment, the present invention relates to a method of reducing the evaporation and/or volatility of a compound of formula (I) respectively to a method of improving the retention of a compound of formula (I), said method comprising admixing a compound of formula (I) with all the definitions and preferences as given herein with silica having an average particle size D(v, 0.5) of ≤320 µm, preferably having a D(v, 0.5) selected in the range of 100 to 320 µm, more preferably in the range of 200 to 310 µm and most preferably in the range of 200 to 300 µm. In a particular preferred embodiment, the silica furthermore exhibits a pH selected in the range of pH 6 to 7 (measured as a 1% suspension in distilled water) as this further increases the retention of the active. In an even more preferred embodiment, the method comprises the preparation of a formulation (I), (II), (III), (IV) or (V) as defined herein, as these formulations are particular suitable to effectively retain the active over storage.

In another embodiment, the present invention relates to method of reducing the evaporation and/or volatility respectively to method of improving the retention of a compound of formula (I), said method comprising the step of preparing a powderous formulation (I), (II), (III), (IV) or (V). Preferably, the powderous formulation exhibits a retention of at least 80%, preferably of at least 85%, most preferably of at least 87%.

The term 'retention' as used herein refers to a retention of the compound of formula (I) with all the definitions and preferences as given herein over a storage time of 12 weeks (open bag; 25° C.; 50% relative humidity (r.H.)).

In a further advantageous embodiment, the invention relates to a method to enhance the retention of a compound of formula (I) with all the definitions and preferences as given herein in a feed product, said method comprising the step of adding the compound of formula (I) in the form of a formulation (I), (II), (III), (IV) or (V) to the feed composition.

In a further embodiment, the invention relates to a method to enhance the storage stability of a feed product comprising a compound of formula (I), respectively reducing the evaporation (volatility) of a compound of formula (I) in a feed product, said method comprising the step of adding the compound of formula (I) in the form of a formulation (I), (II), (III), (IV) or (V) to the feed composition.

Preferably, the amount of the formulation (I), (II), (III), (IV) or (V) in the feed product is selected such, that the amount of the compound of formula (I) is in the range of 0.01 to 50 g/kg of feed product, preferably in the range of 0.02 to 25 g/kg of feed product, most preferably in the range of 1 to 10 g/kg of feed product.

The term feed product refers in particular to ruminant feed compositions as well as to feed additives.

The invention is illustrated by the following Examples. All temperatures are given in ° C. and all parts and percentages are related to the weight.

EXAMPLES

Particle Size Determination:

The methodology described below followed the recommendations outlined in ISO13320-1 for diffraction light scattering techniques.

The particle sizes of various silica grades have been measured by a Malvern Master Sizer 2000 following the recommendation of ISO13320-1 for diffraction light scattering techniques. An aliquot of about 5 grams of the material tempered at 25° C.-35 to 55% r.H is sampled into the vibrator hopper of the dry dispersion unit (Sirocco). The flow aperture of the dispenser gate is set up on the way that the product flows for 30 seconds through the measurement zone using a tygon tube, at a vibration feed rate of 50%. A sample measurement at 0.1 bar of disperser pressure is taken for 30 seconds and a snap of 30000. The sample pass through the focused beams of light (Helium-neon laser for the red light and solid state light source for the blue) and scatter the light allowing a measurement of particles between 0.02 and 2000 micrometers. The medium particle diameter in volume, D(v, 50), is determined using Fraunhofer approximation.

pH Determination of the Silica:

a solution or suspension of distilled water with 1% of the respective silica is prepared. After 5 minutes the solution or suspension is stirred magnetically and measured at room temperature with a standard pH-electrode.

Preparation of the Formulation:

To 80 g of different type of silica grades as outlined in table 1) placed on a beaker, is added 80 g of a 20 wt.-% 3-nitrooxypropanol solution in propyleneglycol under gentle agitation at room temperature. After 5 minutes agitation, the adsorption is completed and a free flowing powder is obtained.

Stability Study:

Two aluminium bags containing 5 g of the respective formulation are stored open at 25° C. under controlled atmosphere (50% r.H). The concentration of 3-nitrooxypropanol was determined by HPLC using an Agilent High Performance Liquid Chromatography 1260 Infinity system, using an Aquasil C18, 150×3 mm, 3 µm column and detecting at 210 nm. The column oven was set to 23° C., the autosampler not temperature controlled. The mobile phase consisted of mobile phase A (940 mL Milli-Q-water+60 ml acetonitrile+1 mL methane sulfonic acid) and mobile phase B (800 ml Milli-Q-water+200 ml acetonitrile+1 mL methane sulfonic acid) which were used in gradient mode (0 min: 0% B, 15 min: 0% B, 15.5 min: 100% B, 21 min: 100% B, 21.5 min: 0% B, 25 min: 0% B (=end of run)) with a flow of 0.4 ml/min. The results (as relative concentration to the initial value set to 100%) are presented Table 1.

TABLE 1

| Silica | | Retention | |
|---|---|---|---|
| Particle size [D(v, 0.5) in µm] | pH | initial | 12 weeks |
| 296 | 6.6 | 100 | 88 |
| 285 | 7.9 | 100 | 87 |
| 224 | 7.0 | 100 | 89 |
| 339 (Reference) | 7.5 | 100 | 77 |

As can be retrieved from table 1, the use of the specific silica according to the present invention results in an improved retention of the active.

The invention claimed is:
1. A storage-stable powderous formulation comprising:
(i) at least 0.1 weight-% (wt-%), based on the total weight of the powderous formulation, of a compound of formula (I):

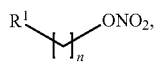

formula (I)

wherein
n is an integer from 1 to 15;
R¹ is selected from the group consisting of H, $C_1$-$C_6$ alkyl, phenyl, —OH, —NH$_2$, —CN, —COOH, —O(C=O)R⁸, —NHC(=O)R⁸, SO$_2$NHR⁸, and —ONO$_2$, and
R⁸ is $C_1$-$C_6$ alkyl, phenyl or pyridyl;
with the proviso that when n is >3 the hydrocarbon chain may be interrupted by —O— or —NH—;
(ii) 0 to 40 wt-%, based on the total weight of the powderous formulation, of an edible oil, and
(iii) at least 25 wt-%, based on the total weight of the powderous formulation, of silica having a particle size D(v, 0.5) of ≤320 μm.

2. The storage-stable powderous formulation according to claim 1 which further comprises:
(iv) 0 to 10 wt-%, based on the total weight of the powderous formulation, of water and/or an additive.

3. The storage-stable powderous formulation according to claim 2, wherein the additive is a thickener selected from the group consisting of gums and/or cellulose derivatives.

4. The storage-stable powderous formulation according to claim 3, wherein the additive is a thickener selected from the group consisting of xanthan gum, karaya gum and/or ethylcellulose.

5. The storage-stable powderous formulation according to claim 1 consisting of
(i) 2 to 20 wt-%, based on the total weight of the powderous formulation, of the compound of formula (I),
(ii) 10 wt-% to 45 wt-%, based on the total weight of the powderous formulation, of the edible oil,
(iii) at least 35 wt-%, based on the total weight of the powderous formulation, of the silica having a D(v, 0.5) of ≤320 μm, and
(iv) 0 to 10 wt-%, based on the total weight of the powderous formulation, of water and/or an additive.

6. The storage-stable powderous formulation according to claim 1, wherein n is an integer between 3 and 9 and R¹ is OH, COOH or —ONO$_2$.

7. The storage-stable powderous formulation according to claim 1, wherein the compound of formula (I) is selected from the group consisting of 3-nitrooxypropanol, 9-nitrooxynonanol, 5-nitrooxy pentanoic acid, 6-nitrooxy hexanoic acid, bis(2-hydroxyethyl)amine dinitrate, 1,4-bis-nitrooxybutane and 1,5-bis-nitrooxypentane.

8. The storage-stable powderous formulation according to claim 1, wherein the edible oil is selected from the group consisting of propyleneglycol, corn oil, rapeseed oil, sunflower oil, middle chain triglyceride (MCT), glycerol and mixtures thereof.

9. The storage-stable powderous formulation according to claim 1, wherein the edible oil is propyleneglycol.

10. The storage-stable powderous formulation according to claim 1 consisting of:
(i) 2 to 12 wt-%, based on the total weight of the powderous formulation, of 3-nitrooxypropanol,
(ii) 20 to 40 wt-%, based on the total weight of the powderous formulation, of propyleneglycol,
(iii) at least 40 wt-%, based on the total weight of the powderous formulation, of the silica having a particle size D(v, 0.5) of ≤320 μm, and
(iv) 0 to 7 wt-%, based on the total weight of the powderous formulation, of water.

11. The storage-stable powderous formulation according to claim 1, wherein the particle size D(v, 0.5) of the silica is a range of 100 to 320 μm.

12. The storage-stable powderous formulation according to claim 1, wherein the particle size D(v, 0.5) of the silica is a range of 200 to 300 μm.

13. The storage-stable powderous formulation according to claim 1, wherein the silica exhibits a pH in a range of 6 to 7.

14. The storage-stable powderous formulation according to claim 1, wherein the formulation contains a coating which is selected from the group consisting of glycerine monostearate, carnauba wax, candelilla wax, sugarcane wax, palmitic acid, stearic acid hydrogenated cottonseed oil, hydrogenated palm oil, hydrogenated rapeseed oil and mixtures thereof.

15. The storage-stable powderous formulation according to claim 1, wherein the formulation exhibits retention of the compound of formula (I) which is at least 80%.

16. The storage-stable powderous formulation according to claim 1, wherein R⁸ is 2-pyridyl.

17. The storage-stable powderous formulation according to claim 1, wherein the particle size D(v, 0.5) of the silica is in a range of 200 to 310 μm.

18. The storage-stable powderous formulation according to claim 1, wherein the formulation exhibits a retention of the compound of formula (I) which is at least 85%.

19. The storage-stable powderous formulation according to claim 1, wherein the formulation exhibits a retention of the compound of formula (I) which is at least 87%.

20. A feed product which comprises the storage-stable formulation according to claim 1.

* * * * *